(12) United States Patent
Brown

(10) Patent No.: US 7,555,470 B2
(45) Date of Patent: Jun. 30, 2009

(54) RESEARCH DATA COLLECTION AND ANALYSIS

(75) Inventor: Stephen J. Brown, Woodside, CA (US)

(73) Assignee: Health Hero Network, Inc., Redwood City, CA (US)

( * ) Notice: Subject to any disclaimer, the term of this patent is extended or adjusted under 35 U.S.C. 154(b) by 0 days.

(21) Appl. No.: 11/599,573

(22) Filed: Nov. 14, 2006

(65) Prior Publication Data

US 2007/0067251 A1    Mar. 22, 2007

Related U.S. Application Data

(63) Continuation of application No. 10/233,296, filed on Aug. 30, 2002, which is a continuation-in-part of application No. 09/799,852, filed on Mar. 5, 2001, now abandoned, which is a continuation of application No. 09/274,431, filed on Mar. 22, 1999, now Pat. No. 6,196,970.

(51) Int. Cl.
    *G06N 5/02* (2006.01)
(52) U.S. Cl. ................ 706/47; 706/62; 706/924; 600/301; 600/481; 600/529
(58) Field of Classification Search ............ 706/45, 706/62, 924, 47; 702/19; 705/2; 600/300, 600/301, 372, 481, 529, 3
    See application file for complete search history.

(56) References Cited

U.S. PATENT DOCUMENTS

| 5,038,800 | A | * | 8/1991 | Oba ............................ 600/509 |
| 5,518,001 | A | * | 5/1996 | Snell ........................... 600/510 |
| 5,675,635 | A |   | 10/1997 | Vos et al. |
| 5,722,418 | A | * | 3/1998 | Bro ............................ 600/545 |
| 5,793,969 | A |   | 8/1998 | Kamentsky et al. |
| 5,796,393 | A |   | 8/1998 | MacNaughton et al. |
| 5,835,896 | A |   | 11/1998 | Fisher et al. |
| 5,875,432 | A |   | 2/1999 | Sehr |
| 5,897,493 | A | * | 4/1999 | Brown ......................... 600/300 |
| 5,935,060 | A | * | 8/1999 | Iliff ............................ 600/300 |
| 5,978,466 | A |   | 11/1999 | Quattrocchi et al. |
| 6,022,315 | A | * | 2/2000 | Iliff ............................ 600/300 |
| 6,024,699 | A | * | 2/2000 | Surwit et al. ................. 600/300 |
| 6,208,974 | B1 | * | 3/2001 | Campbell et al. .............. 705/3 |
| 6,234,965 | B1 | * | 5/2001 | Miller et al. ................. 600/300 |

(Continued)

*Primary Examiner*—David R Vincent
*Assistant Examiner*—Omar F Fernandez Rivas
(74) *Attorney, Agent, or Firm*—Suiter Swantz pc llo

(57) ABSTRACT

The invention provides a method and system by which research data can be collected and analyzed during the course of the research testing, and the research testing itself possibly modified to account for conclusions drawn from the research data. In a first aspect of the invention, a research subject can respond to a protocol stored on a server by manipulating input keys on a remotely located client device onto which a research protocol has been installed. The protocol can include questions concerning the subject's physical or mental well being such as whether their symptoms are relieved or not, or even exacerbated. The protocol can also include calling for data obtained by coupling the client device with another medical device such as a glucose monitor. In a preferred embodiment, the subject is presented with narrowly structured questions and suggested answers provided by the protocol. The set of possible answers is restricted. In the event that a suggested answer is ambiguous, inapplicable or raises new questions, a protocol can present a new question to the subject.

6 Claims, 3 Drawing Sheets

U.S. PATENT DOCUMENTS 6,246,992 B1 * 6/2001 Brown .......................... 705/2
6,248,063 B1 * 6/2001 Barnhill et al. ............. 600/300
6,256,613 B1 * 7/2001 Falchuk et al. ................. 705/2
6,269,339 B1 * 7/2001 Silver ........................... 705/2
6,329,139 B1 12/2001 Nova et al.

* cited by examiner

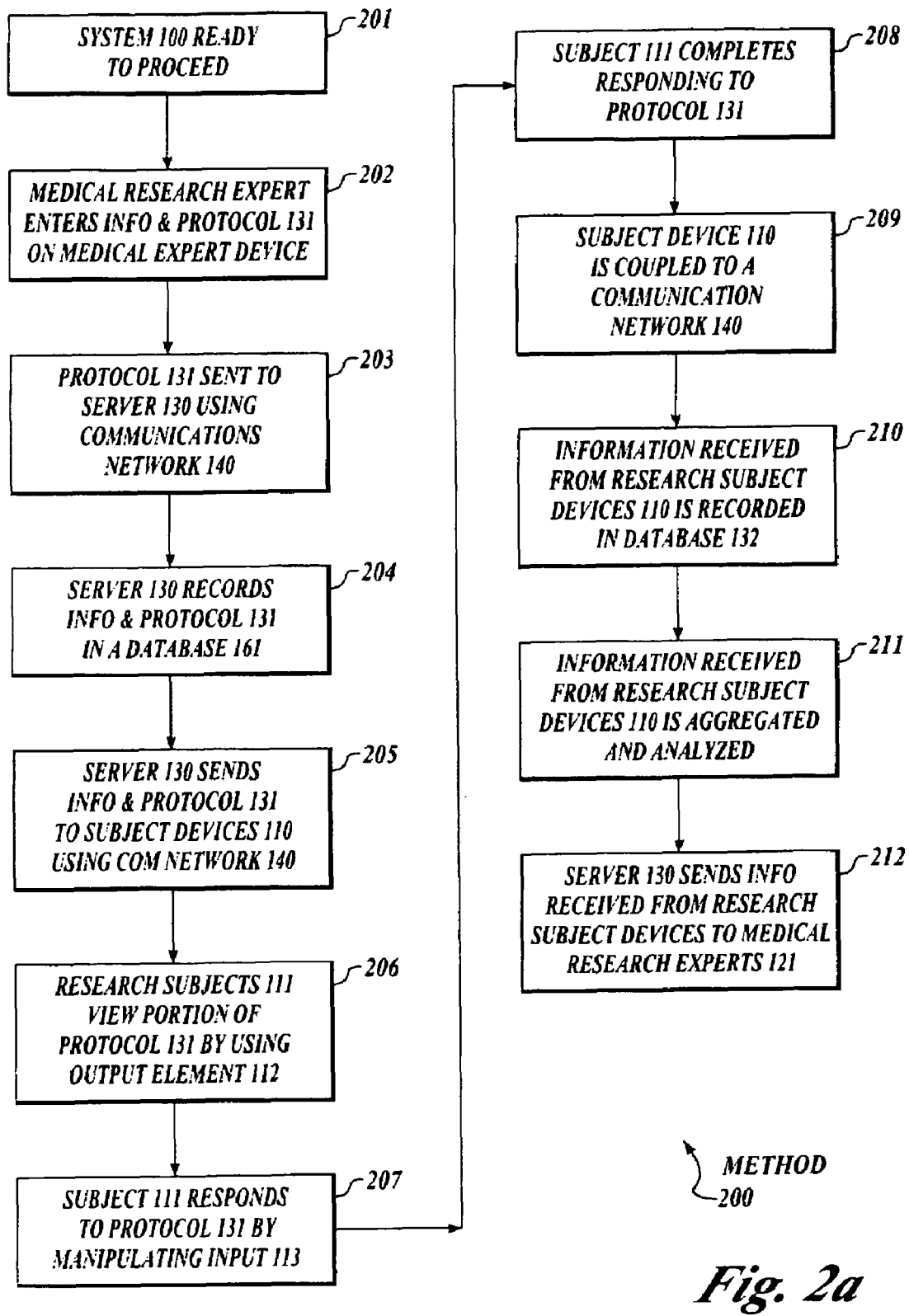

RESEARCH DATA COLLECTION AND ANALYSIS

CROSS REFERENCE TO RELATED APPLICATIONS

The present application is a continuation of U.S. patent application Ser. No. 10/233,296 filed Aug. 30, 2002 which is a continuation-in-part of U.S. patent application Ser. No. 09/799,852 filed Mar. 5, 2001, (abandoned) which is a continuation of U.S. patent application Ser. No. 09/274,431 filed Mar. 22, 1999, now U.S. Pat. No. 6,196,970. Said U.S. patent application Ser. Nos. 10/233,296, 09/799,852 and 09/274,431 are hereby incorporated by reference in their entirety.

FIELD OF THE INVENTION

This invention relates to research data collection and analysis.

BACKGROUND OF THE INVENTION

Human beings are sometimes used as subjects in different types of medical, psychological, and other research. Generally, such research fits into one of several broad categories: academic or industrial research, FDA clinical trials, and marketing and sales research. Human beings are also used as research subjects in experiments designed to correlate genotype and phenotype with drug reactions. For example, a researcher may seek to learn whether patients with the genotype for sickle cell disorder experience greater light sensitivity when taking a specific antibiotic.

Academic and industrial investigators often employ human subjects to learn how humans respond to some pre-determined stimuli such as a drug or a psychological event. For a first example, an academic researcher may use post-menopausal women as subjects in experiments designed to widen our understanding of the neuroendocrine response to ethanol. Many different types of data can be obtained in such experiments. In this first example, a researcher could correlate the data on different hormone levels with blood alcohol levels, the frequency of selected patient behaviors, number of cigarettes smoked and many other possible factors. These data can be aggregated with similar data from other researchers and conclusions can be drawn based upon their observations.

A second area in which human subjects are sometimes used as a research tool involves government approval of new drugs for human patients. The Food and Drug Administration (FDA) approves new drugs that are to be marketed for human consumption. Presently, FDA approval is contingent upon the drug successfully passing three phases of testing during which the drug is blindly administered to human subjects. Taken together, these three phases of testing are called clinical trials. Only those drugs that successfully complete all three phases of clinical trials can be marketed.

In the general course of events, the sponsor of a drug will submit an application and protocol to the FDA for clinical testing. After the application is reviewed and approved, Phase I of clinical testing begins. Experienced clinical investigators administer the drug to a small number of healthy volunteers. Although drug dosage and metabolism may be studied, the main focus of this initial testing phase is drug safety. Since safety concerns are paramount, testing is performed on a relatively small population (between 20 to 100 subjects) for a short period of time. Drugs that induce toxic reactions or other adverse effects do not advance to Phase II. This initial screening eliminates approximately 30% of all applicants.

The main focus of Phase II testing is to determine whether the drug is an effective treatment. Since the focus is on the effectiveness of the drug and the threat of adverse reactions has been largely ruled out, Phase II clinical trials involve a larger number of subjects (up to several hundred) who suffer from a problem the drug is designed to treat. Phase II trials may involve the blind testing of up to several hundred subjects. Only 33% of all drugs advance to phase III testing.

Phase III testing may involve up to several thousand subjects. This phase lasts longer (between one to four years) than either Phase I or Phase II. Here, the safety, dosage and effectiveness of the new drug are all rigorously screened. Between 25-30% of all drugs pass phase III trials and receive the required approval necessary for marketing.

An additional level of testing is also employed. After a new drug has passed all three phases of clinical trials, researchers may also want to learn if any adverse effects occur after the drug is marketed. Thus, additional investigation may involve post-marketing surveillance of patients who have been administered the drug after it is approved by the FDA. Such post marketing surveillance is a useful tool that helps researchers learn more about how patients respond to a specific drug.

Known marketing and sales research includes attempting to elicit responses from human participants regarding whether those participants would be more or less likely to purchase selected goods or services. It is known to attempt to correlate responses with demographic data about the participants (such as age, gender, household income, or residence locale), as well as psychological and other information about participants (such as whether participants are considered ""early adopters").

Known methods for collecting and analyzing data from human subjects in research suffer from several drawbacks. While these methods generally achieve their respective goals of learning more about the human response to various stimuli, screening out ineffective and unnecessarily toxic drugs, and providing useful information for marketing or sales, known methods suffer from several drawbacks and limitations that can make them time-consuming or inefficient.

A first problem in the known art is that collection of data from subjects or participants in research or clinical trials often involves obtaining and analyzing fuzzy assessments from subjects who are not necessarily under the continual observation of a clinician or other personnel. Indeed, many subjects (such as the controls in clinical trials) are not under the care of a physician at all, but merely report to an expert researcher periodically for testing and analysis. Such testing and analysis frequently involves self-reporting a number of parameters. A subject's answer to an inquiry often involves the making of a fuzzy assessment of physical state, mood or quality of life. Accordingly, there is a need for a method to evaluate and standardize such fuzzy self-assessments.

A second problem in the known art is that researchers are unable to respond to incoming data in real time. In known methods, data from research or clinical trials is collected and stored for analysis at a later time. Frequently, researchers or lab technicians enter their observations in a paper copy of a log book or lab notebook. Often these results are entered near the end of an experiment. This practice makes it impossible for an investigator to evaluate the data or change the experimental design. While researchers may have an approximate idea as to the general trend of incoming data, they are frequently unable to respond to that trend until the data is analyzed, well after any opportunity for altering the method of collection or the nature of the data collected. Accordingly, researchers are unable to modify a clinical protocol while in process. This inability to evaluate and respond to incoming data during data collection can create conditions that are dangerous for the subjects of the research. It is believed that morbidity and mortality associated with evaluation of new drugs would be substantially reduced if researchers could respond during the research, such as to halt the clinical trial or adjust the drug dosage. Accordingly, there is a need to evaluate and respond to subjects in real time.

A third problem in the known art is that collection of data from research and clinical trials often calls for the aggregation of data from many different geographical testing sites. It is believed that drug testing and other research would be quicker if there were a way to aggregate data and respond to it in real time, during the time of the trials or research. Accordingly, there is a need to aggregate and analyze data from many remote sites.

A fourth problem in the known art is that identification of subjects in clinical trials who respond to a drug is not always readily apparent because it frequently requires evaluation of many different parameters. Part of this problem involves the nature of disease. In some cases, an acute condition will spontaneously heal, regardless of treatment. Chronic diseases often follow an unpredictable course as symptoms abate for a time and then worsen. Under these conditions, it is often difficult to determine whether the change in the subject's condition may be attributed to the drug or some other factor. Identifying subjects who respond to a drug is particularly problematic in Phase II trials where the issue is the efficacy of the drug. Accordingly, there is a need to be able to distinguish responders from non-responders on the basis of many different factors.

A fifth problem in the known art involves the nature of research with human subjects. Most experiments involving administration of drugs are either blinded or double blinded. In blinded studies, the subject does not know whether they are receiving the active drug or a placebo. In essence, although the investigator knows what the subject is receiving, the subject does not know whether or not they are being used as a control. In double-blinded subjects, neither the researcher nor the research subject is aware of the subject's status. Blinded studies are problematic because researcher may impose his own bias on the incoming data. Double-blinded studies are problematic because the researcher may not be sensitive to phenomena that the subject is experiencing. Another problem raised in double-blinded studies is that the investigator very often becomes unblinded when observing the effect of a drug on a research subject. According, there is a need for an impartial, unbiased observer that remains responsive to the research subjects.

Accordingly, it would be advantageous to provide a technique by which research data can be collected and analyzed during the course of the research testing, and the research testing itself possibly modified to account for conclusions drawn from the research data. For example, it would be advantageous to provide a device that can be carried by a research subject or participant that can be coupled and uncoupled to a communication system that is also accessible to researchers and other remote experts. Such a device would allow researchers to (1) collect, analyze and respond to input from the research subjects or participants in real time, (2) evaluate fuzzy assessments made by a subject or participant by making progressively narrower inquiries designed to obtain specific data, (3) aggregate and analyze data from a large number of remote sites quickly, (4) change the research protocol in response to input from subjects in real time and (5) rapidly identify responders and non-responders by correlating the data with a number of disparate parameters that are not necessarily apparent when the study begins. These advantages are achieved in embodiments of the invention in which a research subject enters data using a client device that is coupled to a server via a communication link.

SUMMARY OF THE INVENTION

The invention provides a method and system by which research data can be collected and analyzed during the course of the research testing, and the research testing itself possibly modified to account for conclusions drawn from the research data. In a first aspect of the invention, a research subject can respond to a protocol stored on a server by manipulating input keys on a remotely located client device onto which a research protocol has been installed. The protocol can include questions concerning the subject's physical or mental well being such as whether their symptoms are relieved or not, or even exacerbated. The protocol can also include calling for data obtained by coupling the client device with another medical device such as a glucose monitor. In a preferred embodiment, the subject is presented with narrowly structured questions and suggested answers provided by the protocol. The set of possible answers is restricted. In the event that a suggested answer is ambiguous, inapplicable or raises new questions, a protocol can present a new question to the subject. This elimination of fuzzy answers imposes a logical structure upon the subjects' assessments.

In a second aspect of the invention, data entered by the subject is relayed using a communication link to a server device. This incoming data can be aggregated with other incoming data from subjects and their associated client devices. In a preferred embodiment, the data is statistically analyzed according to parameters set by the protocol.

In a third aspect of the invention, a remote expert research clinician can review incoming data from either the aggregated population or from individuals as it is being analyzed. Such rapid collection and analysis allows a researcher to change the protocol in response to the trend of the data, correlate different parameters of the data so as to better identify subjects that are responding to treatment and schedule appropriate interventions as needed. The researcher can also identify specific subgroups among the population of subjects, initiate new lines of inquiry and test new sub-hypotheses that may be raised by the incoming data. This includes correlating different drug responses experienced by phenotypically similar subjects with gene expression, and other variables.

FIGS. (2A & 2B) shows a process flow diagram of a method for operating a system for interaction with a community of individuals, including research subjects and investigators.

DETAILED DESCRIPTION OF THE PREFERRED EMBODIMENT

In the following descriptions, a preferred embodiment of the invention is described with regard to preferred process steps and data structures. Embodiments of the invention can be implemented using general-purpose processors or special purpose processors operating under program control, or other circuits, adapted to particular process steps and data structures described herein. Implementation of the process steps and data structures described herein would not require undue experimentation or further invention.

System Elements

Figure 1:
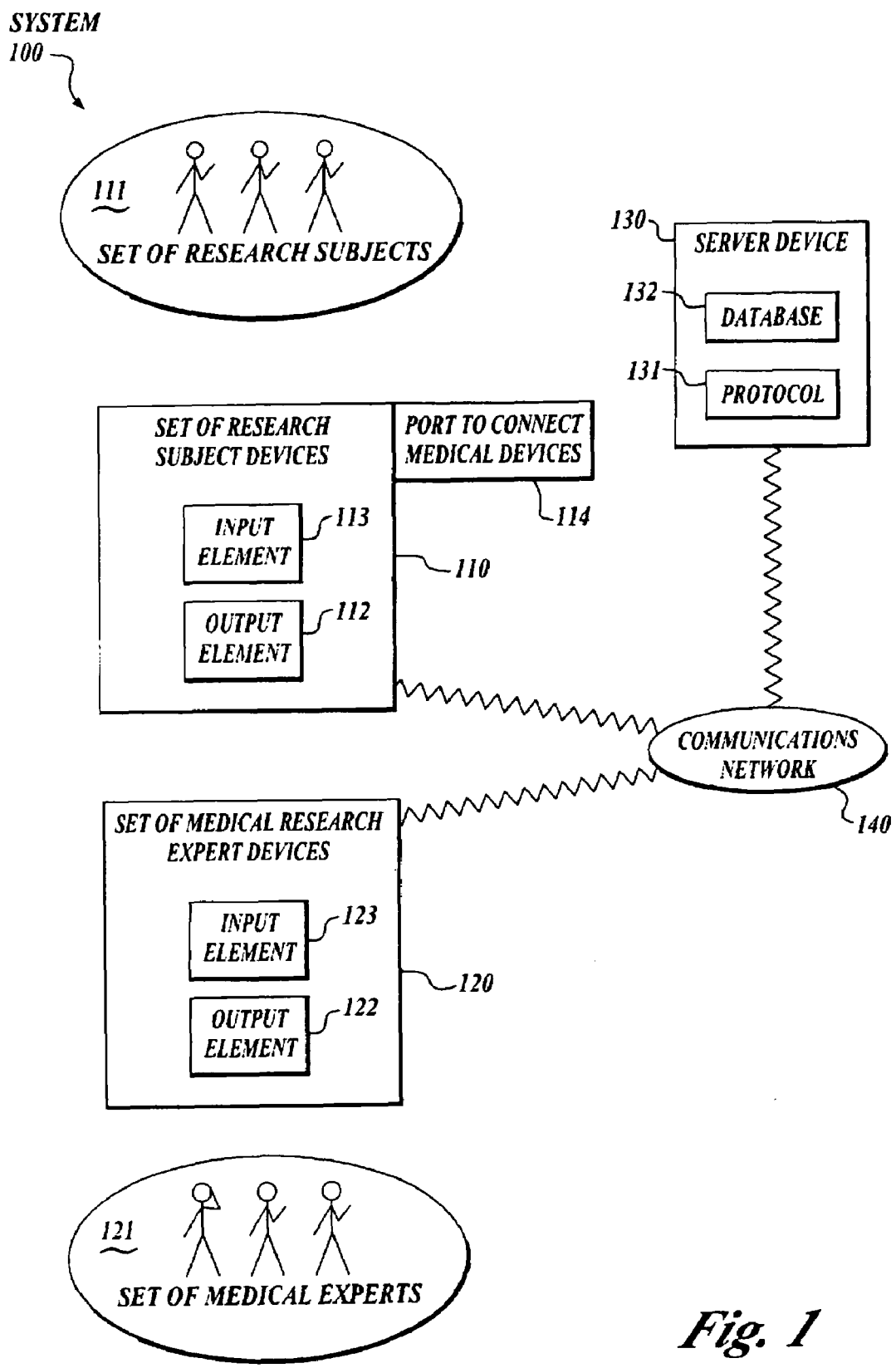
FIG. 1 shows a block diagram of a system 100 to collect and analyze data from human research subjects.

FIG. 1 shows a block diagram of a system 100 to collect and analyze data from human subjects engaged in medical research using a protocol or other intelligent message, which acts in place of a researcher, investigator, clinician or other medical expert.

A system 100 includes a set of subject devices 110, a set of medical research expert devices 120 and a server device 130. The subject device 110, the medical research expert device 120 and the service device 130 are coupled using a communication network 140.

The set of research subject devices 110 is used by a set of research subjects 111. Each research subject device includes an output element 112, an input element 113 and a port 114. The subject 111 manipulates the subject device 110 to send feedback from the subject 111 to the server 130 and to receive information from the protocol 131. Port 114 can be coupled to a variety of medical appliances to send additional data to the server 130.

The set of medical research expert devices 120 is used by a set of medical research experts 121. Each medical expert device includes an output element 122 and an input element 123.

The server device 130 includes a protocol 131 and a database 132.

For further information regarding a data structure and simplified research subject interface, and preferred embodiments of the subject device 110, medical research expert device 120 and the server device 130 including data base 132, see related application Ser. No. 09/201,323, Express Mailing No. EE143637591US, filed Nov. 30, 1998 in the name of Stephen J. Brown, titled "Leveraging Interaction with a Community of Individuals" assigned to the same assignee, and other related applications incorporated by reference therein.

For further information regarding the protocol or other intelligent message used by the system, see related application Ser. No. 09/203,882, Express Mailing No. EE143637565US, filed Dec. 1, 1998, in the name of Stephen, J. Brown, titled ""Remote User Data Collection Protocols Including Data Structures and User Interface," assigned to the same assignee, and other related applications incorporated by references therein.

For information regarding a medicine dispenser which can be used by the system, see related application Ser. No. 09/203, 880, Express Mail Mailing No. EE143637557US, filed Dec. 1, 1998, in the name of Stephen J. Brown, et al., titled ""Using a Computer Communication System with Feedback to Dispense Medicine," assigned to the same assignee, and other related applications incorporated by reference therein.

For information regarding genotype and phenotype correlation, see related U.S. Pat. No. 5,985,559, Express Mail Mailing No. EI113824573US, filed May 3, 1998 in the name of Stephen J. Brown, et al. titled ""System and Method for Preventing, Diagnosing and Treating Genetic and Pathogen-Caused Disease", assigned to the same assignee, and application Ser. No. 09/041,809, Express Mail Mailing No. EE262620680US, filed Mar. 13, 1998 in the name of Stephen J Brown, et al. titled "Phenoscope and Phenobase" assigned to the same assignee.

Method of Operation

Figure 2B:
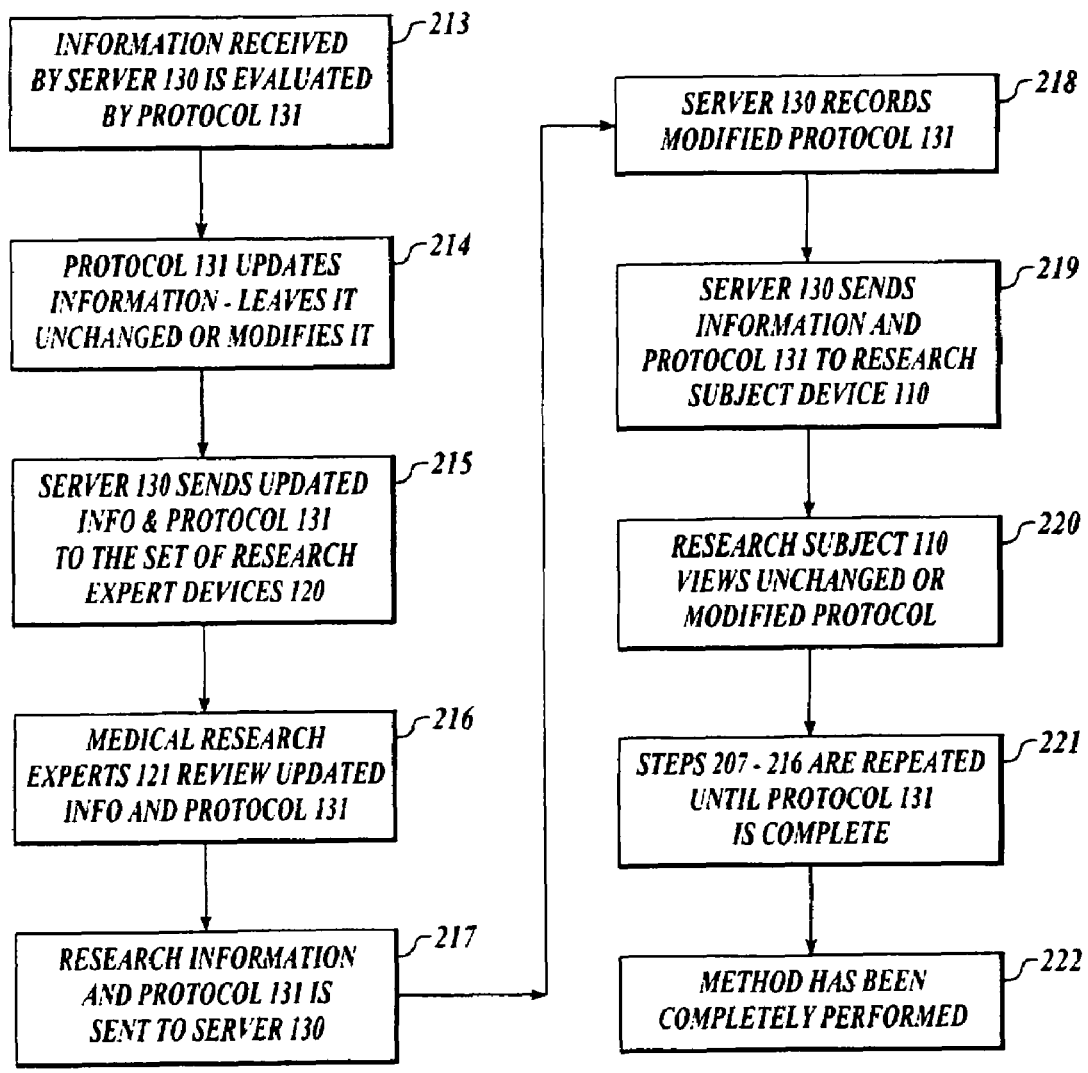

FIG. 2 shows a process flow diagram of a method for collecting data from human research subjects to be performed by the system and for analyzing and reporting that data to research experts.

A method 200 is performed by a system 100, as follows:

At a flow point 201, the system 100 is ready to proceed.

At a step 202, a medical research expert 121 enters information concerning the type of data to be collected from a set of subjects 111 and a protocol 131 on a medical research expert device 120.

At a step 203, the research information and protocol 131 entered onto the medical research expert device 120 is sent to a server device 130 using the communication network 140.

At a step 204, the server device 130 records the research information and protocol 131 submitted by the medical research expert 121 in the database 132.

At a step 205 in a preferred embodiment, the server device 130 sends the research information and protocol 131 to a set of research subject devices 110 using the communication network 140. In alternative embodiments, the server device 130 may send the research and protocol 131 information to other medical research experts 121 for review.

At a step 206 the set of research subjects 111 view some portion of the protocol 131 that was sent to the set of research subject devices 110 by looking at a presentation screen or other output element 112 contained in the research subject device 110.

At a step 207, the set of subjects 111 respond to the protocol 131 sent to the set of research subject devices 110 by manipulating a keypad or other input 113 included in the research subject device 110. Alternatively, the set of subjects 111 respond to the protocol 131 sent to them by coupling the subject device 110, using a port 114 included in the research subject device 110, to a medical appliance such as one or more of, or some combination of, the following: a blood glucose meter, an oxymeter, a peak flow meter, a blood pressure gauge, a weight scale, a pulse sensor, a home infusion system, a CPAP sleep apnea device, a location sensing device, a digital video camera or a drug dispensing apparatus.

At a step 208, the research subject 111 has completed responding to the protocol 131.

At a step 209, the subject device 110 is coupled to a communication network 140 which sends the information entered by the subject 111 in response to the protocol 131 to the server device 130.

At a step 210 the information received by the server device 130 is recorded in the database 132.

At a step 211, the information received from the research subject devices 110 is aggregated and statistically analyzed.

At a step 212, in a preferred embodiment, the server device 130 sends the information received from the research subject devices 110 to the various medical research experts 121. In an alternative embodiment, the server device 130 does not send the information. The information remains available on the server device 130 where it can be looked up by interested parties.

At a step 213, the information received by the server device 130 from the research subject device 110 is evaluated by the protocol 131.

At a step 214, the protocol 131 updates the research information and either leaves it unchanged or modifies it in accordance with the protocol logic.

At a step 215, in a preferred embodiment, the server device 130 sends the updated research information and protocol 131 to the set of research expert devices 121 using the communication network 140. In an alternative embodiment, the server device 130 does not send the updated research information to the medical research expert device 120.

At a step 216, the medical research expert 121 review the updated information and protocol 131 and the other information input by the set of research subjects 111 and either leave the updated research information and protocol unchanged or modify it as necessary. In an alternative embodiment, step 216 does not take place.

At a step 217, in a preferred embodiment, the research information and protocol 131 as unchanged or modified by the medical research expert(s) 121 is sent to the server device 130 using the communications network 140. In an alternative embodiment, step 217 does not take place.

At a step 218, the server device 130 records the modified research and protocol 131 information sent by the medical research expert 121 in the database 132. In an alternative embodiment, step 218 does not take place.

At a step 219 in a preferred embodiment, the server device 130 sends the research and protocol 131 information as unchanged or as modified by the medical research expert 121 to the research subject device 110 using the communication network 130. In an alternative embodiment, step 219 does not take place.

At a step 220, the research subject 111 views the unchanged or modified protocol, as they did in step 206.

At a step 221, the method repeats steps 207 through 216 until all desired information is obtained from the subject and the protocol 131 has been completed. After sending the information to the medical research expert(s) for final review (step 216), the information resides in the database and the method is complete.

At a step 222, the method has completely performed a system 100.

Alternative Embodiments

Although preferred embodiments are disclosed herein, many variations are possible which remain within the concept, scope and spirit of the invention, and these variations would become clear to those skilled in the art after perusal of this application.

What is claimed is:

1. A method, comprising:
   transmitting a protocol for data retrieval regarding a plurality of human subjects, said protocol being transmitted to a plurality of devices, said protocol being transmitted during a course of research testing of a human response to a pre-determined stimuli, said protocol including at least one question or request for information regarding physical well being or mental well being;
   receiving data in response to said protocol from each device of said plurality of devices, each device of said plurality of devices being associated with a single human subject;
   aggregating data collected from each device of said plurality of devices;
   determining a trend in said received data amongst a plurality of human subjects;
   identifying a subset of said plurality of human subjects based upon said trend in said received data;
   generating an updated protocol to be sent to said subset of said plurality of human subjects, said updated protocol being modified from said protocol to include at least one additional question or request for information regarding physical well being or mental well being to correlate different parameters of the data received from each device of said plurality of devices;
   receiving data in response to said updated protocol from each device associated with said subset of said plurality of human subjects; and
   displaying said data in response to said updated protocol from each device associated with said subset of said plurality of human subjects on a presentation device.

2. An apparatus, comprising:
   a plurality of input devices for collecting data related to human subjects, each input device of said plurality of input devices being configured based upon a protocol, said data being collected during a course of research testing of a human response to a pre-determined stimuli, said protocol including at least one question or request for information regarding physical well being or mental well being;
   a server device relatively remote from said input devices for receiving said data, said server device storing said protocol;
   a communication link between each input device and said server device;
   a processor including software configured to determine trend a amongst a plurality of human subjects based on said data in real-time with receipt of said data related to the plurality of human subjects from said plurality of input devices and generate an updated protocol to be sent to said subset of said plurality of human subjects; and
   a presentation device relatively remote from said server device and coupled to said processor, wherein said presentation device is configured to present said data in response to said updated protocol, said updated protocol being modified from said protocol to include at least one additional question or request for information regarding physical well being or mental well being to correlate different parameters of the data received from each device of said plurality of devices.

3. The apparatus as claimed in claim 2, wherein said plurality of input devices collects data based upon said protocol.

4. The apparatus as claimed in claim 2 wherein each device of said plurality of input devices includes a medical device.

5. The apparatus as claimed in claim 4, wherein said medical device includes a blood glucose meter, an oxymeter, a peak flow meter, a blood pressure gauge, a weight scale, and a pulse sensor.

6. The apparatus as claimed in claim 2 wherein each device of said plurality of input devices includes at least one of a location sensing device or a camera.

* * * * *